(12) United States Patent
Tonon et al.

(10) Patent No.: US 8,580,733 B2
(45) Date of Patent: Nov. 12, 2013

(54) SITE-SPECIFIC MONOCONJUGATED INSULINOTROPIC GLP-1 PEPTIDES

(75) Inventors: Giancarlo Tonon, Pula (IT); Gaetano Orsini, Gallarate (IT); Mauro Sergi, Padova (IT); Rodolfo Schrepfer, Vila Guardia (IT); Pierandrea Esposito, Barcelona (ES)

(73) Assignee: Bio-Ker SRL, Milan (IT)

( * ) Notice: Subject to any disclaimer, the term of this patent is extended or adjusted under 35 U.S.C. 154(b) by 0 days.

(21) Appl. No.: 12/998,708

(22) PCT Filed: Nov. 4, 2009

(86) PCT No.: PCT/EP2009/064599
§ 371 (c)(1),
(2), (4) Date: Jul. 22, 2011

(87) PCT Pub. No.: WO2010/057774
PCT Pub. Date: May 27, 2010

(65) Prior Publication Data
US 2011/0281797 A1    Nov. 17, 2011

(30) Foreign Application Priority Data
Nov. 20, 2008 (IT) .............................. MI2008A2066

(51) Int. Cl.
*A61K 38/00* (2006.01)
*A61P 3/10* (2006.01)

(52) U.S. Cl.
USPC .............................. 514/7.2; 514/6.8; 514/6.9

(58) Field of Classification Search
None
See application file for complete search history.

(56) References Cited

U.S. PATENT DOCUMENTS

| | | | |
|---|---|---|---|
| 4,179,337 | A | 12/1979 | Davis et al. |
| 5,545,618 | A | 8/1996 | Buckley et al. |
| 5,985,265 | A | 11/1999 | Kinstler et al. |
| 6,010,871 | A | 1/2000 | Takahara et al. |
| 2005/0181985 | A1 | 8/2005 | Hemberger et al. |
| 2007/0166278 | A1 | 7/2007 | Veronese et al. |
| 2008/0113905 | A1* | 5/2008 | DiMarchi et al. ............... 514/12 |

FOREIGN PATENT DOCUMENTS

| | | |
|---|---|---|
| EP | 0785276 | 7/1997 |
| EP | 1068301 | 7/2006 |
| EP | 0944648 | 3/2007 |
| WO | WO 03/074087 | 9/2003 |
| WO | WO 03074087 | 9/2003 |
| WO | WO 2005070468 | 8/2005 |
| WO | WO 2005099769 | 10/2005 |
| WO | WO 2007000468 | 1/2007 |

OTHER PUBLICATIONS

Veronese et al., DDT 10: 1451-1458, 2005.*
Bowie et al., 1990, Science 247: 1306-1310.*
Wells, 1990, Biochemistry 29:8509-8517.*
Adelhorst, K., et al "Structure-activity studies of glucagon-like peptide-1", The Journal of Biological Chemistry,269, (9) 6275-6278, 1994.
Ando H. et al "Purfication and characterisation of a novel transglutaminase derived from micro-organisms." Agric. Biol. Chem. 53(10): 2613-2617, 1989.
Bloom M., "Albugon fusion protein: a long-acting analog of GLP-1 that provides lasting antidiabetic effect in animals." Diabetes, vol. 52, p. A112, 2003.
Choi S, at al. "Control of blood glucose by novel GLP-1 delivery using biodegradable triblock copolymer of PLGA-PEG-PLGA in type 2 diabetic rats." Pharm Res. May 2004:21(5):827-31.
Coussons PJ, et al. "Factors that govern the specificity of transglutaminase-catalysed modification of proteins and peptides." Biochem J. Mar. 15, 1992;282 ( Pt 3):929-30.
Davison MB, et al. "Exenatide", Nat Rev Drug Disoov. Sep. 2005;4(9):713-4.
Delgado C, et al., "The uses and properties of PEG-linked proteins.", Crit Rev Ther Drug Carrier Syst. 1992:9(3-4):249-304.
Drucker DJ., et al. "Minireview: the glucagon-like peptides.", Endocrinology. Feb. 2001;142(2):521-7.
Eng J, et al "Isolation and characterization of exendin-4, an exendin-3 analogue, from *Heloderma suspectum* venom. Further evidence for an exendin receptor on dispersed acini from guinea pig pancreas.", J Biol Chem. Apr. 15, 1992;267(11):7402-5.
Esposito C, et al. "Mammalian transglutaminases, Identification of substrates as a key to physiological function and physiopathological relevance.", FEBS J, Feb. 2005;272(3):615-31.
Fontana A., et al. "Site-specific modification and PEGylation of pharmaceutical proteins mediated by transglutaminase.", Advanced Drug Delivery Reviews 60: 13-28, 2008.
Gallwitz B. et al, "Structure/Activity Characterization of Glucagon-Like Peptide-1." Eur J. Biochem. 225: 1151-1156, 1994.
Greenwald RB et al "Effective drug delivery by PEGylated drug conjugates.", Adv Drug Deily Rev. Feb. 10, 2003;55(2):217-50.
Holst JJ., et al "The physiology of glucagon-like peptide 1.", Physiol Rev. Oct. 2007;87(4):1409-39.
Jorgensen L,et al, "Preparing and evaluating delivery systems for proteins." Eur J Pharm Sci. Nov. 2006;29(3-4):174-82. Epub May 25, 2006.
Kaiser E. T., "Synthetic approaches to biologically active peptides and proteins including enzymes", Accounts of Chemical Research 22: 47-54, 1989.
Kinstler OB, et al., "Characterization and stability of N-terminally PEGylated rhG-CSF." Pham Res. Jul. 1996;13(7):996-1002.
Knudson LB, et el., "Potent derivatives of glucagon-like peptide-1 with pharmacokinetic properties suitable for once daily administration." J Med Chem. May 4, 2000;43(9):1664-9.
Kobayashi K, et al., "Molecular cloning of the transglutaminase gene from *Bacillus subtilis* and its expression in *Escherichia coli.*", Biosci Biotechnol Biochem. Jun. 1998;62(6):1109-14.
Kobayashi K. et al., "M-(γ-Glutamyl)lysine cross-links of spore coat proteins and transglutaminese activity in *Bacillus subtilis*." FEMS Microbiology Letters 144; 157-160, 1996.

(Continued)

Primary Examiner — Gyan Chandra
(74) Attorney, Agent, or Firm — Hueschen and Sage

(57) ABSTRACT

The present invention is related to glucagon-like peptide-1 (GLP-1) and analogues insulinotropic peptides, monoconjugated to biocompatible polymeric molecules by enzymatic direct and site-specific transglutamination reaction as well as their pharmaceutical formulations and delivery systems for therapeutical application in dismetabolic pathologies such as type 2 diabetes.

15 Claims, 4 Drawing Sheets

(56) References Cited

OTHER PUBLICATIONS

Kohane D. S., "Microparticles and nanoparticles for drug delivery.", Biotechnology and Bioengineering 96:203-209, 2007.

Lee K Y et al. "Polymeric protein delivery systems." Prog Polym Sci. 2007;32:669-697.

Lee S-H, et al., "Synthesis, characterization, and pharmacokinetic studies of PEGylated glucagon-like peptide-1." Bioconjugate Chem 16:377-382 2005.

Merrifield B., "Solid phase synthesis.", Science. Apr. 18, 1986;232(4748):341-7.

Miranda I P, et al. "Design and synthesis of conformationally constrained glucagon-like peptide-1 derivatives with increased plasma stability and prolonged in vivo activity." J Med. Chem 51:2758-2765, 2008.

Muller RH, et al., "Challenges and solutions for the delivery of biotech drugs—a review of drug nanocrystal technology and lipid nanoparticles.", J Biotechnol. Sep. 30, 2004;113(1-3):151-70.

Nucci M L, et al., "PEGylation increases the stability of proteins." Advanced Drug Delivery Reviews 6:133-151, 1991.

Ohtsuka T, et al. "Comparison of substrate specificities of transglutaminases using synthetic peptides as acyl donors.", Biosci Biotechnol Biochem. Dec. 2000;64(12):2608-13.

Ohtsuka T, et al., "Substrate specificities of microbial transglutaminase for primary amines.", J Agric Food Chem. Dec. 2000;48(12):6230-3.

Parveen S. et al., "Nanomedicine: clinical applications of polyethylene glycol conjugated proteins and drugs.", Clin Pharmacokinet. 2006;45(10):965-88.

Pastor MT, at al., "Addressing substrate glutamine requirements for tissue transglutaminase using substance P analogues.", FEBS Lett. May 28, 1999;451(3):231-4.

Ritzel U, et al., "A synthetic glucagon-like peptide-1 analog with improved plasma stability." J Endocrinol. Oct. 1998;159(1):93-102.

Roberts MJ, et al., "Chemistry for peptide and protein PEGylation.", Adv Drug Rev. Jun. 17, 2002;54(4):459-76.

Sato H., "Enzymatic procedure for site-specific pegylation of proteins.", Adv Drug Deliv Rev. Jun. 17, 2002;54(4):487-504.

Sato H., "Transglutaminase-Mediated Dual and Site-Specific Incorporation of Poly(ethyleneglycol) Derivatives into a Chimeric Interleukin-2," Bioconjugate Chem 11:502-509, 2000.

Schmaljohann D., "Thermo- and pH-responsive polymers in drug delivery.", Adv Drug Deliv Rev. Dec. 30, 2006;58(15):1655-70. Epub Oct. 18, 2006.

Schnabel CA, et al., "Immunogenicity of xenopeptide hormone therapies." Peptides. Jul. 2006;27(7):1902-10. Epub Mar. 3, 2006.

Singh S. et al. "Thermosensitive polymers: synthesis, characterization and delivery of proteins" International Journal of Pharmaceutics 341: 68-77 2007.

Sinha VR, et al., Biodegradable microspheres for protein delivery., J Control Release. Jul. 31, 2003;90(3):261-80.

Thornton K, et al., "Structure of glucagon-like peptide (7-36) amide in a dodecylphosphocholine micelle as determined by 2D NMR." Biochemistry. Mar. 29, 1994;33(12):3532-9.

Uckaya G, et al., "Improvement of metabolic state in an animal model of nutrition-dependent type 2 diabetes following treatment with S 23521, a new glucagon-like peptide 1 (GLP-1) analogue." J Endocrinol. Mar. 2005;184(3):505-13.

Yokoyama KI et al., "Overproduction of microbial transglutamines in *Escherichia coli*, in vitro refolding, and characterization of the refolded form." Biosci Biotechnol Biochem. Jun. 2000;64(6):1263-70.

Youn YS, et al., "Evalution of therapeutic potentials of site-specific PEGylated glucagon-like peptide-1 isomers as a type 2 anti-diabetic treatment: insulinotropic activity, glucose-stabilizing capability, and proteolytic stability." Biochem Pharmacol. Jan. 1, 2007;73(1):84-93. Epub Sep. 17, 2006.

Zalipsky, "Chemistry of polyethylene glycol conjugates with biologically active molecules", Advanced Drug Delivery Reviews, vol. 16, Issues 2-3, Sep. 1995. pp. 157-182.

\* cited by examiner

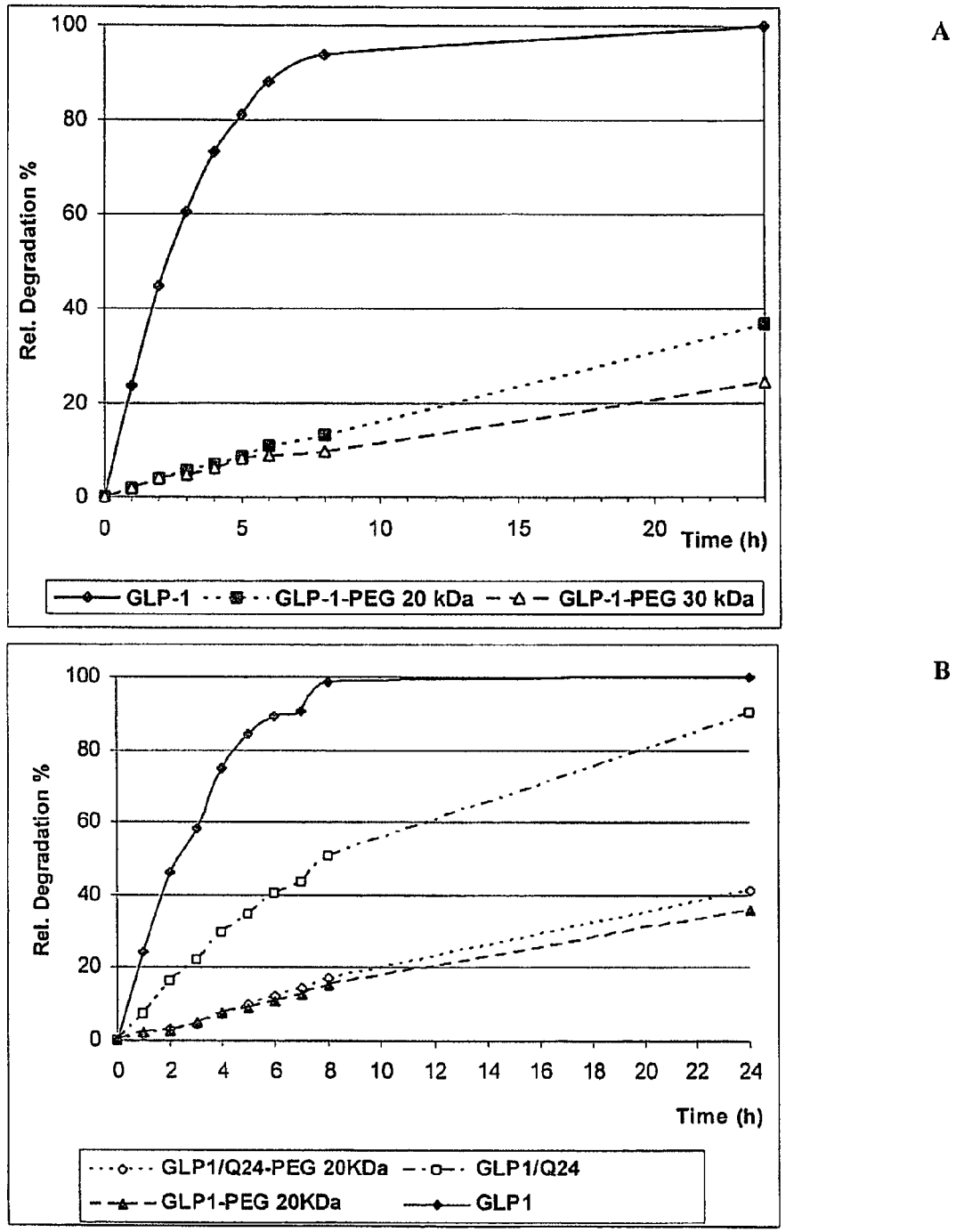
Figure 1: In vitro DPP-IV degradation profiles of GLP-1-amide (♦); Q17N-A24Q-GLP-1-amide ( ) and the corresponding 20 kDa monopegylated derivatives of GLP-1-amide (▼) and Q17N-A24Q-GLP-1-amide (◊).

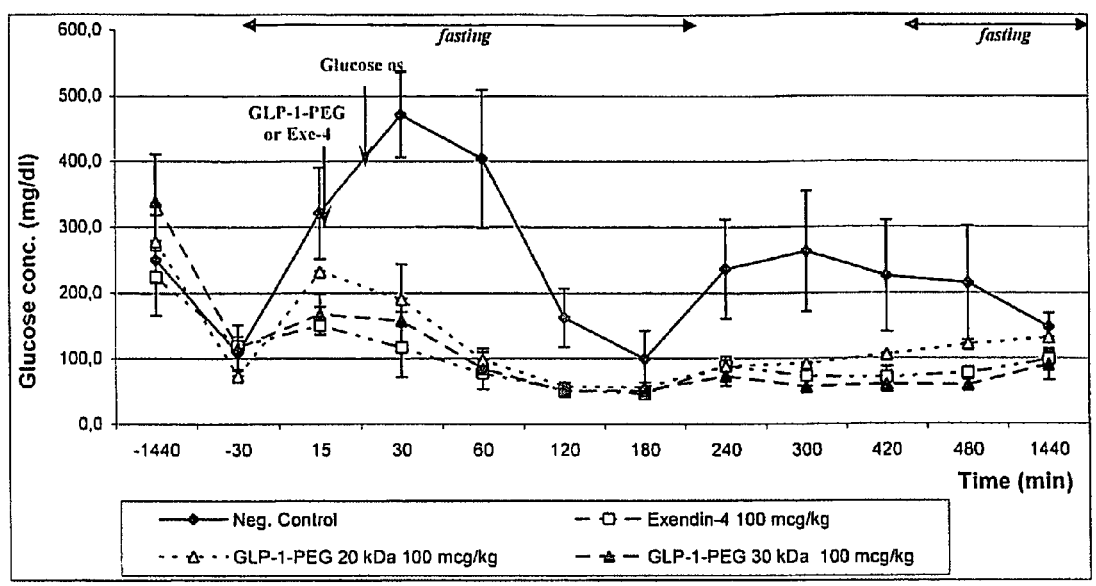
Figure 2: Glucose-stabilizing profile in type-2 diabetic db/db mice after intraperitoneal administration of 20 kDa (Δ) and 30 kDa (▲) Q17-monopegylated GLP-1-amide and Exenatide (□) (time −30 min, 100μ/kg) and the oral administration of glucose (time 0 min; 1.5g/kg).

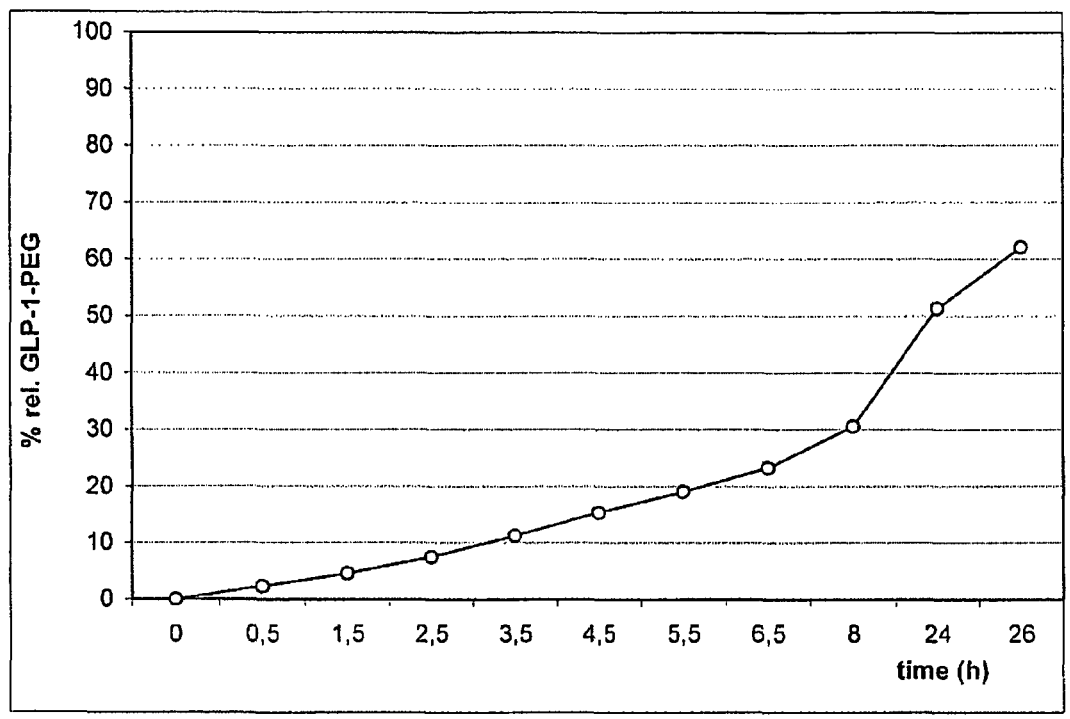
Figure 3: *In vitro* release of 20 kDa monopegylated GLP-1-amide from a thermoreversible gel preparation containing 22% of Poloxamer 407 incubated at 37°C in phosphate buffer.

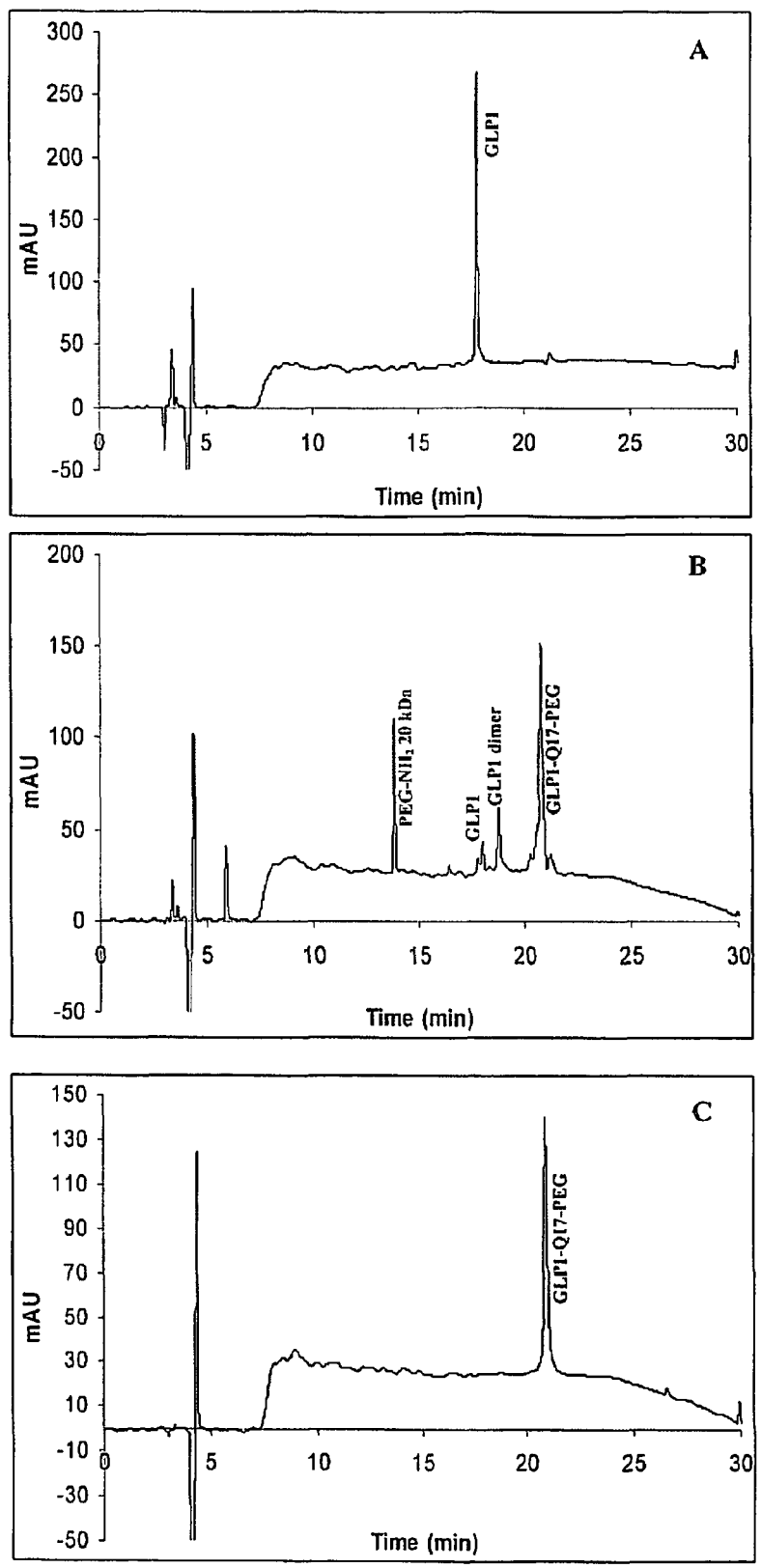
Figure 4 : RP-HPLC analysis of native GLP-1-amide (panel A), reaction mixture of direct pegylation of GLP-1-amide with 20 kDa m-PEG-amino catalyzed by M-Tgase after 16 hours at room temperature (panel B) and GLP1-amide-Q17-PEG 20kDa purified by ion-exchange column chromatography (panel C).

SEQUENCE LISTING

```
<160> NUMBER OF SEQ ID NOS: 2

<210> SEQ ID NO 1
<211> LENGTH: 30
<212> TYPE: PRT
<213> ORGANISM: Homo sapiens
<220> FEATURE:
<221> NAME/KEY: Amide
<222> LOCATION: (30)..(30)
<223> OTHER INFORMATION: The aminoacid in position 30 is amidated, i.e.
      the C-terminal residue is an amide and not a carboxy group
<220> FEATURE:
<221> NAME/KEY: Amide
<222> LOCATION: (30)..(30)
<223> OTHER INFORMATION: The aminoacid in position 30 is an amidated
```

```
                    arginine, i.e. the C-terminal residue is an amide and not a
                    carboxy group

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Xaa
            20                  25                  30

<210> SEQ ID NO 2
<211> LENGTH: 31
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

SITE-SPECIFIC MONOCONJUGATED INSULINOTROPIC GLP-1 PEPTIDES

The present invention is related to glucagon-like peptide-1 (GLP-1) and analogues insulinotropic peptides, monoconjugated to biocompatible polymeric molecules by enzymatic direct and site-specific transglutamination reaction as well as their pharmaceutical formulations and delivery systems for therapeutical application in dismetabolic pathologies such as type 2 diabetes.

FIELD OF THE INVENTION

Diabetes mellitus is a disease that has been known to exist for thousands of years and that currently afflicts more than 200 million people worldwide. In addition to the decrease of life expectancy and lower quality of life of individuals with diabetes, the disease and its associated complications are a major burden on health budgets.

The more common form of diabetes is Type 2 diabetes (or non-insulin-dependent diabetes mellitus) which has both genetic and environmental components and represents a multifactorial, heterogeneous group of disorders, which results from defects in insulin secretion, insulin action, or both. and leads to uncontrolled or elevated levels of blood glucose.

In industrialized countries, approximately 90% of individuals with diabetes have type 2 diabetes whose prevalence has increased dramatically over the past several decades most likely under the influence of diet and physical activity level modifications.

Type 2 diabetes usually occurs in overweight adults over the age of 45; however, the incidence of Type 2 diabetes in overweight children (usually over the age of 10) is also increasing rapidly.

Current therapies in the management of type 2 diabetes include lifestyle intervention through diet modification and physical exercise, and treatment with oral or injected hypoglycemic agents; however, not all individuals with type 2 diabetes respond in the same way to these treatments.

A better understanding of physiological responses to meals enabled the discovery of incretin hormones and the development of new agents whose therapeutic action is based on the enhancement of gastrointestinal hormone action [Drucker D J, 2001].

These therapies are associated with slowing of gastric emptying, stimulation of insulin and inhibition of glucagon secretion, improved control of postprandial hyperglycemia, and control of body weight.

Incretins are gut-derived hormones released by nutrients that potentiate insulin secretion under elevated glycemic conditions. Human glucagon-like peptide-1 (GLP-1) is a prototypical incretin hormone, originated from preproglucagon gene and secreted from enteroendocrine L-cells of the intestine after food intake, exhibiting a potent blood glucose-lowering effect through different physiological mechanisms including the secretion of endogenous insulin in a glucose-dependent manner, the decrease of blood glucagon levels and the reduction of gastric emptying by slowing gastric motility. Besides, GLP-1 stimulates the proliferation and differentiation of new pancreas β-cells leading to increase of β-cell mass [Hoist J J, 2007].

The major form of circulating human GLP-1 is a C-terminal amidated peptide of 30 aminoacid residues generally indicated as GLP-1(7-36)-amide (SEQ ID NO 1); a minor non-deamidated and C-terminally glycine extended form of 31 aminoacid residues, generally indicated as GLP-1 (7-37), is also detectable in blood (SEQ ID NO 2). Both peptides display the same biological activities and are equipotent. For the purposes of the present invention, as shown by SEQ IDs NO 1 and 2, GLP-1 peptides and their analogues are reported according to peptide chain numeration starting from the N-terminal histidine residue.

```
                                            SEQ ID 1
GLP-1(7-36)amide:

1            11           21
HAEGTFTSDV   SSYLEGQAAK   EFIAWLVKGR-CONH₂

SEQ ID 2
Glycine extended GLP-1(7-37)

1            11           21           31
HAEGTFTSDV   SSYLEGQAAK   EFIAWLVKGR   G-COOH
```

The insulinotropic action of GLP-1 peptides and analogues, that is the stimulation of insulin secretion only when plasma glucose levels are above the normal physiological value, makes these compounds potential candidates for the treatment of type 2 diabetes. GLP-1 peptides exert their biological effects through seven transmembrane G-protein-coupled receptors expressed in the β-cell of the islets of Langerhans as well as in gastrointestinal tract and other tissues including heart, kidney, lungs and brain. Studies of structure-activity relationship of GLP-1 peptides carried out by alanine scanning mutagenesis demonstrated that positions 1, 4, 6, 7, 9, 13, 15, 22, 23 and 26 are critical for receptor binding [Adelhorst K, et al., 1994; Gallwitz B et al., 1994].

Examples of GLP-1 analogues include exendin-3 and exendin-4, two 39-aminoacid peptides originally isolated from the venom of Gila monster (*Heloderma suspectum*), which share approximately 50% sequence identity to GLP-1 itself and are indeed agonists of GLP-1 receptor. A synthetic preparation of exendin-4 (exenatide) has been approved in both USA and Europe as adjunctive therapy to for the treatment of type 2 diabetes based on two daily subcutaneous injections [Davidson M B et al., 2005].

Unfortunately, the therapeutic use of GLP-1 peptides is limited by a very short plasma half-life (for example GLP-1-amide has a $t_{1/2}<1.5$ minute after intravenous administration) mainly due to rapid degradation by plasma dipeptidyl peptidase IV (DPP-IV) or CD26, a serine-type protease that cleaves N-terminal dipeptides from polypeptide chains after a proline or alanine residue. The biological activity of natural circulating GLP-1 peptides is in fact regulated by the N-terminal DPP-IV-mediated cleavage at the alanine-2 residue to give the inactive metabolite des-His-Ala-GLP-1 peptide.

Even exenatide, which differs from GLP-1 in N-terminal position 2 which confers DPP-IV resistance and is therefore essentially eliminated by glomerular filtration, when injected intravenously displays a half-life in plasma of about 30 minutes.

The rapid inactivation and/or clearance of GLP-1 peptides and analogues has stimulated interest in long-acting degradation-resistant GLP-1 receptor agonists exhibiting prolonged duration of action with respect to natural GLP-1 peptides after in vivo administration. Examples of these GLP-1 derivatives are extensively reported in both scientific and patent literature; they can be obtained, among others, according to the following approaches:

a) by selective amino acids substitutions in GLP-1 peptidic chain that confer DPP-IV resistance as, for example, by replacement of the second N-terminal amino acid L-alanine with D-alanine or serine resulting in GLP-1 analogues which maintain the insulinotropic activity with a significant increase of plasma stability and in vivo half-life [Uçkaya G et al., 2005; Ritzel U et al., 1998; Buckley D I et al., U.S. Pat. No. 5,545,618]

b) by attaching of one or more lipophilic substituents to the side chains of aminoacid residues of GLP-1 and GLP-1 analogues where the lipophilic substituents comprise 4 to 40 carbon atoms and are chemically conjugated to aminoacids both directly or through a spacer. Some of these GLP-1 analogues derivatized with lipophilic moieties showed a protracted profile of action in vivo and higher persistance in plasma compared to natural GLP-1 (Knudsen L et al., EP0944 648)

c) by exploiting naturally occurring insulinotropic peptides such as, for example, exendin-3 and exendin-4 (or its corresponding synthetic form exenatide), two 39 amino acid peptides originally isolated from salivary glands of lizards [Eng J et al., 1992] which were found to be potent GLP-1 receptor agonists. Exenatide, whose therapeutic efficacy was also demonstrated in patients with type 2 diabetes, shares about 50% sequence identity with GLP-1 while differs in N-terminal position 2 where alanine is substituted by a glycine residue, which confers DPP-IV-resistance and a comparatively longer half-life without reducing biological activity.

However, therapeutical administration of human peptides bearing amino acid substitutions and/or additions as well as of peptides of non-human origin, such as exanatide, may raise undesired immune response that may decrease the drug efficacy or induce adverse events in patients, as reported, for example, in clinical studies showing that exenatide treatment for 30 weeks induced the formation of anti-exenatide antibodies in more than 40% of patients [Schnabel C A et. 2006].

d) by chemical conjugation of GLP-1 peptides to poly(ethylene glycol) (PEG) to give derivatives with prolonged biological life-time due to increased proteolytic resistance and, in some cases, diminished glomerular filtration. Site specific monopegylated GLP-1 peptides could be prepared by selective chemical pegylation with propionaldehyde functionalized monomethoxy-PEG (m-PEG) carried out at pH 4.5 on the α-amino group of N-terminal $His^1$ residue; however the resulting mono-pegylated GLP-1, although resistant to DPP-IV degradation, was shown to have little biological activity in vitro [Lee S H et al. 2005].

A favorable balance between resistance to peptidase degradation and insulinotropic activity was shown for GLP-1-amide monopegylated on $Lys^{20}$ residue as well as for GLP-1-amide monopegylated on $Lys^{28}$ which were prepared by a multi-step chemical synthesis including maleic anhydride protection of lysine ε-amino groups, chromatographic separation of $Lys^{20}$- and $Lys^{28}$-protected GLP-1 isomers, chemical pegylation carried out independently on each isomer by reaction of free lysine ε-amino group with 2 kDa m-PEG functionalized with succinimidyl propionate followed by removal of protecting maleic group [Youn Y S et al., 2007].

While these degradation-resistant GLP-1 analogues prolong the half-life of GLP-1 peptides from a few minutes to a few hours, their therapeutic application for the treatment of diabetes still require once- or twice-daily injections so that there is still a need to develop long-acting agents exhibiting a more prolonged circulating half-life and requiring a reduced frequency of parenteral administrations. Examples of these approaches are known in the art and include, among others:

a) acylated derivatives of human GLP-1 or its analogues, as for example liraglutide or {$Arg^{28}$-$Lys^{20}$-N-[ε-(γ-Glu{N-α-hexadecanoyl})]-GLP-1} in which the acyl moiety promotes in vivo serum albumin binding and prolongs the half-life to about 13-15 hours without reduction of potency [Knudsen L B et al., 2000].

b) DPP-IV resistant GLP-1 peptides covalently linked through recombinant DNA technology to a large plasma protein as, for example, human albumin, to give a GLP-1-albumin fused protein or Albugon which displays a half-life of 3 days in monkeys [Bloom M. et al., 2003]

c) by entrapment of GLP-1 peptides in biodegradable polymers which act as a depot for delivering GLP-1 at sustained and controlled release rates [Choi A et al., 2004]

In the present invention we address the problem of long-lasting insulinotropic peptides through the preparation of GLP-1 peptides and GLP-1 peptide analogues monoconjugated to biocompatible polymers by enzymatic direct site-specific transglutamination reaction as well as of their pharmaceutical formulations and delivery systems useful for therapeutical application in type 2 diabetes.

BRIEF DESCRIPTION OF THE DRAWINGS

FIG. 1. (A) In vitro DPP-IV degradation profiles of GLP-1-amide (◆); and the monopegylated derivatives. GLP-1-PEG 20 kDa (▲) and GLP-1-PEG 30 kDa (Δ). (B) In vitro DPP-IV degradation profiles of GLP-1-amide (◆): Q17N-A24Q-GLP-1-amide (□) and the corresponding 20 kDa monopegylated derivatives of GLP-1-amide (▲) and Q17N-A240-GLP-1-amide (◇).

FIG. 2. Glucose-stabilizing profile in type-2 diabetic db/db mice after intraperitoneal administration of 20 kDa (Δ) and 30 kDa (▲) Q17-monopegylated GLP-1-amide and Exenatide (□) (time −30 min, 100 μg/kg) and the oral administration of glucose (time 0 min; 1.5 g/kg).

FIG. 3. In vitro release of 20 kDa monopegylated GLP-1-amide from a thermoreversible gel preparation containing 22% of Poloxamer 407 incubated at 37° C. in phosphate buffer.

FIG. 4. RP-HPLC analysis of native GLP-1-amide (panel A), reaction mixture of direct pegylation of GLP-1-amide with 20 kDa m-PEG-amino catalyzed by M-Tgase after 16 hours at room temperature (panel B) and GLP 1-amide-Q17-PEG 20 kDa purified by ion-exchange column chromatography (panel C).

DESCRIPTION OF THE INVENTION

The present invention relates to polymer-conjugated incretin mimetic peptides, such as GLP-1 peptides, and their analogues and derivatives characterized, with respect to natural peptides, by maintenance of therapeutical useful biological activity, resistance to peptidase degradation and longer circulating half-life. These new compounds are obtained by site-specific monoconjugation to biocompatible polymers through a direct transglutaminase (Tgase) catalyzed reaction both on a glutamine residue naturally present on incretin mimetic peptides, such as GLP-1 peptides, or on a glutamine residue introduced into the GLP-1 peptidic chains in substitution of other naturally present residues or on a glutamine residue added to the GLP-1 peptidic chains.

For the purposes of the present invention, the term incretin mimetic peptides means a compound that mimics the action of the naturally occurring incretin hormone GLP-1 by enhancing glucose-dependent insulin secretion and related glucose-lowering actions such as, for example, inhibition of glucagon release following meals, slowing the rate of gastric emptying and promotion of satiety.

It is well-known that the conjugation of peptide or protein molecules to high molecular weight biocompatible hydrophilic polymers modifies the physico-chemical properties of the resulting conjugated complexes largely maintaining the biological function of the original non-conjugated molecule, such as for example the capability of receptors recognition. In the same time, the conjugation of proteins and peptides with a polymeric moiety may hamper physical contact between the protein and both specific and non specific proteolytic enzymes preventing or reducing the enzymatic proteolysis. Well-known polymeric moieties that have been used in the conjugation of therapeutic proteins are linear or branched poly(ethylene glycol) (PEG) chains with molecular weight between about 2 kDa and 60 kDa. Covalent conjugation of such polymers to one or more residues in the protein molecule modifies a number of functional aspects of the conjugated complexes including, for example, the renal clearance thanks to the increase of apparent molecular size, the stability towards enzymatic degradation as well as the reduction of immunogenicity due to the masking of immunogenic epitopes on the protein surface. There is an increased interest in developing poly(ethylene glycol)-conjugated (pegylated) therapeutic proteins because of their improved stability and their more favorable pharmacokinetics profile enabling lower dose-frequency than their non-pegylated counterparts [Greenwald R B et al., 2003].

Examples of therapeutic proteins commercially available as pegylated derivatives are, among others, PEG-Interferon-alpha, used for the treatment of patients infected with the hepatitis C virus, PEG-Filgrastim (PEG-granulocyte-colony stimulating factor), that stimulates the granulocytes production and differentiation in bone marrow, and Pegvisomant, a pegylated human growth hormone receptor antagonist which is indicated for the treatment of acromegaly [Parveen S and Sahoo S K, 2006].

Methods for chemical conjugation of proteins and peptides with PEG are known in the art as exemplified by the following basic references: Davis F F et al., U.S. Pat. No. 4,179,337; Veronese et al, WO2005099769; Nucci M L et al., 1991; Delgado C et al., 1992; Zalipski S, 1995; Roberts M J et al., 2002.

Pegylated therapeutic proteins, as any other drug, should ideally be homogeneous products with well defined structural and functional characteristics. However, chemical pegylation of proteins are based on non specific reactions with nucleophilic residues (most commonly the s-amino group of surface lysine residues or the side-chain carboxylic groups) and produces different extent of conjugation and/or mixtures of pegylated positional isomers each of them could give rise to variations in characteristics relevant to clinical application including biological activity and appearance of side-effects.

In some cases, it is possible to prepare essentially site-specific monopegylated proteins by exploiting the preferential reactivity, at acidic pH, of the alpha-amino group of N-terminal residue with aldehyde-functionalized monomethoxy-PEG (m-PEG) chains followed by reductive alkylation [Kinstler O B et al., U.S. Pat. No. 5,985,265], as applied to produce the N-terminal monoconjugated PEG-filgrastim marketed as a long-lasting form of G-CSF [Kinstler O B et al., 1996].

Unfortunately, the application of the above mentioned N-terminally selective chemical pegylation to GLP-1 peptides give site specific monopegylated derivatives devoided of biological activity due to the fact that the N-terminal histidine residue is involved in the receptor binding and activation; on the other hand, the selective chemical pegylation of one of the two lysine residues of GLP-1-peptides to give biologically active monopegylated derivatives either on Lys[20] residue or on Lys[28] was only possible through a low-yield, complex and multi-step method involving chemical protection of lysine s-amino groups, chromatographic separation of Lys[20] and Lys[28] protected GLP-1 isomers, conventional independent chemical pegylation of each isomer followed by removal of protecting group from the non reacted lysine residue [Youn Y S et al. 2007].

A potential way to overcome the limitations of the above reported chemical approaches and to prepare site-specific monoconjugated GLP-1 peptides and GLP-1 derivatives and analogues with biocompatible polymers is to exploit the application of the selective transglutaminase catalyzed conjugation between biocompatible polymers functionalized with a primary amino group and a single glutamine residue contained in GLP-1 like peptides.

Transglutaminases (E.C. 2.3.2.13; protein-glutamine γ-glutamyltransferase; Tgase) are enzymes of both eukaryotic and prokaryotic origin which catalyze an acyl transfer reaction between a γ-carboxyamido group of protein-bound glutamine residue and an ε-aminogroup of a lysine residue or a variety of primary amines, in particular straight chain alkylamines, according to the following reaction scheme:

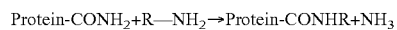

where —$CONH_2$ is the γ-carboxamide group of a protein-bound glutamine residue acting as acyl donor and R—$NH_2$ represents a variety of primary amines (including an ε-aminogroups of lysine residues in the protein chain) acting as acyl acceptor.

The currently known eukaryotic transglutaminases include, among others, the blood coagulation factor XIIIa, the keratinocyte Tgase (type 1 Tgase) and the ubiquitous tissue type Tgase (type 2 Tgase). The various eukaryotic Tgases belong to a family of isoenzymes composed of several subunits and sharing a high degree of both sequence similarity and functional properties, with molecular masses of about 75-90 kDa and a similar $Ca^{2+}$-dependent catalytic mechanism of action [Esposito C and Caputo I, 2004].

More recently, prokaryotic transglutaminases were found in *Streptomyces* and *Bacillus* strains, as well as in various other microorganisms [Ando H et al., 1989; Kobayashi K et al., 1996], and also cloned and expressed as recombinant proteins [Kobayashi K et al., 1998; Yokoyama K et al., 2000; Fuchsbauer H et al., EP1068301]. With respect to eukaryotic Tgases, microbial Tgases (M-Tgases) are monomeric enzymes with a molecular mass of about 38-40 kDa and a $Ca^{2+}$ independent catalytic activity.

Both mammalian and microbial Tgases act with a specific selectivity on side-chain of glutamine residues of proteins representing the acyl donor moiety while much lower or no selectivity was displayed towards the primary amino group representing the acyl acceptor moiety. In fact, both Tgases react not only with the ε-amino groups of lysine residues on protein chains, but also with compounds bearing a primary amino group or with aliphatic alkylamines, preferably with primary aliphatic amines on a linear chain of at least four carbon atoms [Ohtsuka T et al., 2000].

Besides, although the basis for glutamine specificity in Tgases catalyzed reaction remains unknown, there are indications that the microenvironment surrounding the target glutamine can influence its capability to act as Tgases substrate; for example, it has been reported that positively charged or sterically cumbersome side chains preceding or following a glutamine residue, can positively influence recognition on the enzyme part [Cousson P J et al., 1992; Ohtsuka T et al., 2000]; on the other hand, protein sequence having the glutamine residue flanked by both two positively charged residues or two proline residues hamper the correct interaction with Tgases [Pastor M T et al., 1999].

Although no specific consensus site has been identified around the glutamine residues modified by Tgases catalyzed reaction, it is commonly believed that both mammalian and microbial Tgases are able to recognizes as substrate glutamine residues located on solvent accessible, flexible and locally unfolded region of the protein chain encompassing that glutamine residues [Fontana A et al., 2008].

Based on these characteristics, both prokaryotic and eukaryotic Tgase catalyzed reactions have been applied to site-selective incorporation of amino functionalized molecules into proteins, including alkyl-amino functionalized m-PEG chains as reported in patent literature [see for examples, Takahara Y, EP785276; Takahara Y et al., U.S. Pat. No. 6,010,871] and in scientific papers [Sato H et al., 2000; Sato H, 2002] which describe the use of transglutaminases to covalently bind polymer chains to peptides and proteins with at least one glutamine residue in their aminoacid sequence, where glutamines can be both naturally present in the protein chain or inserted by site-specific mutagenesis.

Besides, according to the above disclosed examples, these Tgase catalyzed conjugation reactions were carried out in the presence of a significant excess of the primary amino group functionalized m-PEG substrates (which were present in about 100-1000 fold molar excess) with respect to the glutamine-containing protein substrates. These conditions represent obvious economical and technical drawbacks when the enzymatic conjugation process has to be performed on industrial scale, in particular with high molecular weight amino-functionalized polymers as, for example, with 20-60 kDa alkylamino-m-PEG which are both expensive and difficult to manipulate at such high concentrations.

As far as the Tgase catalyzed pegylation of GLP-1-peptides is concerned a recent patent application [Johansen L et al., WO070468] teaches a two step method to overcome these limitations: in the first step a small functionalized chemical moiety is transferred on the single glutamine residue of GLP-1-peptides by action of both mammalian and microbial Tgases and the resulting intermediate functionalized glutamine is in turn chemically conjugated with a m-PEG chain bearing a reactive group capable to react with the functional group previously introduced by Tgase catalysis. Since the first step involves a low molecular weight compound, its use in large excess in the enzymatic transglutaminase reaction can easily be handled.

We have now surprisingly found, and it represents the main objective of the present invention, that GLP-1 peptides and insulinotropic GLP-1 analogues and derivatives bearing a single glutamine residue can be conjugated directly to alkylamino functionalized polymers with high yields; the term "directly" is herein used to indicate that the covalent bond occurs "directly" between the GLP-1 peptide and the alkylamino functionalized polymer, that is without the need of any intermediate linker. Preferably these alkylamines can be linear or branched m-PEG of molecular weight from 2 to 50 kDa, preferably from 5 to 40 kDa, more preferably from 10 to 30 kDa, even more preferably from 15 to 25 kDa; in the preferred embodiment, the m-PEG has a molecular weight of about 20 kDa. Such polymers are conjugated by a direct enzymatic reaction catalyzed by a transglutaminase, preferably a microbial transglutaminase (M-Tgase), with a molar ratio between alkylamino functionalized polymers and GLP-1 like peptides comprised between 1:1 and 1:100, preferably between 1:5 and 1:35, more preferably between 1:15 and 1:25; according to a most preferred embodiment, it is about 1:20. Also surprisingly, and contrary to the teaching of WO070468, we have found that only M-Tgase is able to catalyze a direct conjugation reaction between m-PEG-amines and GLP-1 peptides or insulinotropic GLP-1 analogues while no enzymatic conjugation of GLP-1 derivatives could be obtained when a mammalian transglutaminase, such as guinea pig-liver Tgase, was used to catalyze the transfer of amino functionalized polymers on the single glutamine residue of GLP-1 like peptides or exenatide substrates The results of some experimental studies of direct enzymatic mono-pegylation of GLP-1-amide and exenatide are summarized in tables 1 and 2.

TABLE 1

Examples of direct transglutaminase-catalyzed site-specific monopegylation of GLP-1-amide.

| GLP-1 mg/ml | GLP-1/mPEG-NH2 molar ratio | mPEG-NH2 MW | Tgase | Buffer | Temp °C. | Monopegylated GLP-1 Yield % |
|---|---|---|---|---|---|---|
| 0.5 | 1/20 | 20 kDa | M-Tgase 0.25 U/ml | $KH_2PO_4$ 10 mM pH 7.4 | 25 | 60% |
| 0.5 | 1/20 | 20 kDa | M-Tgase 0.25 U/ml | $KH_2PO_4$ 10 mM pH 7.4 + 10% DMSO | 25 | 55% |
| 0.5 | 1/20 | 20 kDa | M-Tgase 0.25 U/ml × 2 (*) | $KH_2PO_4$ 10 mM pH 7.4 + 10% DMSO | 25 | 58% |
| 0.5 | 1/20 | 20 kDa | M-Tgase 0.25 U/ml | $KH_2PO_4$ 100 mM pH 7.4 | 25 | 56% |
| 0.5 | 1/20 | 20 kDa | M-Tgase 0.25 U/ml | $KH_2PO_4$ 100 mM pH 7.4 + 10% DMSO | 25 | 33% |
| 0.5 | 1/20 | 20 kDa | M-Tgase 0.25 U/ml | $KH_2PO_4$ 100 mM pH 7.4 + 10% DMSO | 37 | 31% |
| 0.5 | 1/20 | 20 kDa | M-Tgase 0.25 U/ml | $KH_2PO_4$ 10 mM pH 7.4 | 4 | 44% |
| 0.5 | 1/20 | 20 kDa | M-Tgase 0.25 U/ml | $KH_2PO_4$ 10 mM pH 7.4 + 10% DMSO | 4 | 30% |
| 0.5 | 1/20 | 20 kDa | M-Tgase 0.25 U/ml | $KH_2PO_4$ 10 mM pH 7.4 | 37 | 55% |
| 0.5 | 1/20 | 20 kDa | M-Tgase 0.25 U/ml | $KH_2PO_4$ 10 mM pH 7.4 + 5% DMSO | 25 | 55% |
| 0.5 | 1/20 | 20 kDa | M-Tgase 0.25 U/ml | Na citrate 10 mM pH 8.0 | 25 | 60% |
| 0.5 | 1/20 | 20 kDa | M-Tgase 0.25 U/ml | Tris HCl 100 mM pH 7.5 | 25 | 51% |

TABLE 1-continued

Examples of direct transglutaminase-catalyzed site-specific monopegylation of GLP-1-amide.

| GLP-1 mg/ml | GLP-1/mPEG-NH2 molar ratio | mPEG-NH2 MW | Tgase | Buffer | Temp °C. | Monopegylated GLP-1 Yield % |
|---|---|---|---|---|---|---|
| 0.5 | 1/20 | 20 kDa | M-Tgase 0.25 U/ml | Tris HCl 50 mM pH 7.5 | 25 | 58% |
| 0.5 | 1/20 | 20 kDa | M-Tgase 0.5 U/ml | $KH_2PO_4$ 10 mM pH 7.4 | 25 | 60% |
| 0.5 | 1/20 | 20 kDa | M-Tgase 0.5 U/ml | $KH_2PO_4$ 10 mM pH 7.4 + 10% DMSO | 25 | 57% |
| 0.5 | 1/20 | 20 kDa | M-Tgase 0.5 U/ml | $KH_2PO_4$ 10 mM pH 7.4 + 10% DMSO | 4 | 54% |
| 0.5 | 1/20 | 20 kDa | M-Tgase 0.5 U/ml | $KH_2PO_4$ 100 mM pH 7.4 + 10% DMSO | 25 | 44% |
| 0.5 | 1/20 | 20 kDa | M-Tgase 0.5 U/ml | $KH_2PO_4$ 100 mM pH 7.4 + 10% DMSO | 4 | 28% |
| 0.3 | 1/20 | 30 kDa | M-Tgase 0.5 U/ml | $KH_2PO_4$ 10 mM pH 7.4 | 25 | 36% |
| 0.3 | 1/20 | 42 kDa | M-Tgase 0.5 U/ml | $KH_2PO_4$ 10 mM pH 7.4 | 25 | 21% (53% in 24 h) |
| 0.3 | 1/20 | 30 kDa | M-Tgase 0.5 U/ml | $KH_2PO_4$ 100 mM pH 7.4 | 25 | 43% |
| 0.3 | 1/20 | 42 kDa | M-Tgase 0.5 U/ml | $KH_2PO_4$ 10 mM pH 7.4 | 37 | 31% |
| 0.5 | 1/20 | 20 kDa | guinea pig Tgase 0.25 U/ml | Tris 50 mM pH 8 – $CaCl_2$ 10 mM | 25 | No PEGylation |
| 0.5 | 1/20 | 20 kDa | guinea pig Tgase 0.5 U/ml | Tris 50 mM pH 8 – $CaCl_2$ 10 mM | 25 | No PEGylation |
| 0.5 | 1/20 | 20 kDa | guinea pig Tgase 0.3 U/ml | Tris 50 mM pH 7.5 – $CaCl_2$ 10 mM | 25 | No PEGylation |
| 0.5 | 1/20 | 20 kDa | guinea pig Tgase 0.3 U/ml | Tris 100 mM pH 7.5 – $CaCl_2$ 10 mM | 25 | No PEGylation |
| 0.5 | 1/500 | 5 kDa | guinea pig Tgase 0.3 U/ml | Tris 50 mM pH 7.5 – $CaCl_2$ 10 mM | 25 | No PEGylation |
| 0.25 | 1/500 | 5 kDa | guinea pig Tgase 0.3 U/ml | Tris 50 mM pH 7.5 – $CaCl_2$ 10 mM | 25 | No PEGylation |
| 0.25 | 1/500 | 5 kDa | guinea pig Tgase 0.3 U/ml | Tris 50 mM pH 7.5 – $CaCl_2$ 10 mM | 37 | No PEGylation |

(*) A second aliquot of 0.25 U/ml of M-Tgase added after 6 hours
All reactions were conducted for 16 hours.

TABLE 2

Examples of direct transglutaminase-catalyzed site-specific monopegylation of exenatide.

| Exenatide mg/ml | Exenatide/mPEG-NH2 molar ratio | mPEG-NH2 MW | Tgase | Buffer | Temp °C. | Monopegylated Exenatide Yield % |
|---|---|---|---|---|---|---|
| 0.5 | 1/20 | 20 kDa | M-Tgase 0.25 U/ml | $KH_2PO_4$ 10 mM pH 7.4 | 25 | 58% |
| 0.5 | 1/20 | 20 kDa | guinea pig Tgase 0.25 U/ml | Tris 50 mM pH 8 – $CaCl_2$ 10 mM | 25 | No PEGylation |
| 0.5 | 1/20 | 20 kDa | guinea pig Tgase 0.5 U/ml | Tris 50 mM pH 8 – $CaCl_2$ 10 mM | 25 | No PEGylation |

All reactions were conducted for 16 hours.

It is therefore the main objective of the present invention to provide a method for the direct M-Tgase-catalyzed reaction between a single glutamine residue contained in GLP-1-peptides and in insulinotropic GLP-1 analogues and an amino functionalized biocompatible polymer, such as for example linear or branched alkylamino m-PEG of molecular weight from 2 to 60 kDa, to give monoconjugated derivatives acting as incretin mimetics in that they are able to display in vivo biological activities similar to the biological activities of natural incretin hormones.

Another embodiment of the present invention is represented by GLP-1 peptides monoconjugated by M-Tgase-catalyzed direct reaction with biocompatible polymers on the single glutamine residue naturally present in the position 17 of GLP-1-amide or C-terminal glycine extended GLP-1 or on the single glutamine residue naturally present in the position 13 of exenatide.

Combining the fact that GLP-1 peptides and analogue insulinotropic peptides have no defined structure in aqueous solution [Thornton K and Gorenstein D G, 1994] with the reported capability of Tgases to recognize as substrate glutamine residues located on solvent accessible, flexible and locally unfolded region of the protein chain [Fontana A et al., 2008] one could expect that glutamine residues introduced into the peptidic chain of Q17N-GLP-1-peptides and Q17N-GLP-1 analogues would provide alternative substrates for the direct M-Tgase catalyzed monoconjugation reaction with biocompatible polymers. Unexpectedly, however, when a number of these Q17N-GLP-1 glutamine-containing variants including, for example, derivatives with a single glutamine substitution in positions 2, 5, 8, 11, 12 and 24 were reacted with amino functionalized m-PEG in the presence of M-Tgase it was surprisingly found that all mutants but A24Q/Q17N-GLP-1 were not substrates of M-Tgase and consequently, with the exception of A24Q/Q17N-GLP-1 monopegylated on the single glutamine residue in position 24, they did not give the expected monopegylated derivatives as reported, for example, in table 3.

b) bearing glutamine substitution in a position enabling it to act as acyl donor in direct M-Tgase-catalyzed transglutaminase reaction.

GLP-1 peptides and GLP-1 peptide analogues and derivatives, which are used according to the present invention as substrates for the site-specific direct M-Tgase catalyzed mono-pegylation reaction can be prepared by conventional chemical methods well known in the art, such as by solid-phase peptide synthesis or by condensation reaction of peptide fragments as previously disclosed (see for example Merrifield B, 1986 and Kaiser E T, 1989 which are incorporated by reference herein).

Alternatively, GLP-1 peptides and GLP-1 peptide analogues and derivatives, including Q17N-GLP-1 analogues bearing glutamine substitution in any residue not involved in receptor binding and in position enabling them to act as M-Tgase acyl donor substrate, used according to the present invention, can also be prepared by recombinant DNA technologies according to methods well known in the art and previously disclosed (see for example Sambrock J et al., 1989 which is hereby incorporated by reference).

The direct enzymatic reactions of the present invention are carried out by dissolving GLP-1 peptides or GLP-1 peptide analogues and derivatives in a suitable aqueous buffer at pH

TABLE 3

Examples of direct M-Tgase catalyzed site-specific monopegylation of some Q17N-GLP-1-amide mutants.

| Q17N-GLP-1 Mutant | Q17N-GLP-1 mg/ml | Q17-GLP-1/mPEG-NH2 Ratio | mPEG-NH2 MW | M-Tgase U/ml | Buffer | Temp °C. | Result Yield |
|---|---|---|---|---|---|---|---|
| A2Q | 0.5 | 1/20 | 20 kDa | 0.25 | $KH_2PO_4$ 10 mM pH 7.4 | 25 | No PEGylation |
| A2Q | 0.5 | 1/20 | 20 kDa | 0.25 | Na citrate 10 mM pH 7.4 NaCl 0.15M/EDTA 20 mM | 25 | No PEGylation |
| T5Q | 0.5 | 1/20 | 20 kDa | 0.25 | Na citrate 10 mM pH 7.4 NaCl 0.15M/EDTA 20 mM | 25 | No PEGylation |
| S11Q | 0.5 | 1/20 | 20 kDa | 0.25 | Na citrate 10 mM pH 7.4 NaCl 0.15M/EDTA 20 mM | 25 | No PEGylation |
| S12Q | 0.5 | 1/20 | 20 kDa | 0.25 | Na citrate 10 mM pH 7.4 NaCl 0.15M/EDTA 20 mM | 25 | No PEGylation |
| A24Q | 0.5 | 1/20 | 20 kDa | 0.25 | Na citrate 10 mM pH 7.4 NaCl 0.15M/EDTA 20 mM | 25 | MonoPEGylation on Q24 yield 45% |
| A24Q | 0.5 | 1/20 | 20 kDa | 0.25 | $KH_2PO_4$ 10 mM pH 7.4 | 25 | MonoPEGylation on Q24 yield 40% |
| A24Q | 0.5 | 1/20 | 20 kDa | 0.25 | Na citrate 10 mM pH 7.4 NaCl 0.15M/EDTA 20 mM | 25 | MonoPEGylation on Q24 yield 56% |
| A24Q | 0.5 | 1/20 | 20 kDa | 0.25 | $KH_2PO_4$ 10 mM pH 7.4 | 25 | MonoPEGylation on Q24 yield 50% |
| A24Q | 0.5 | 1/20 | 20 kDa | 0.25 | Na citrate 10 mM pH 8.0 | 25 | MonoPEGylation on Q24 yield 60% |

All reactions were conducted for 16 hours.

Another embodiment of the present invention is represented by monoconjugated Q17N-GLP-1-amide and insulinotropic Q17N-GLP-1-peptide analogues obtained by direct M-Tgase catalyzed reaction with biocompatible polymers on a single glutamine residue introduced in substitution of any residue which is both:

a) not involved in receptor binding of the GLP-1-peptides, that is to say any residue but the ones in position 1, 4, 6, 7, 9, 13, 15, 22, 23 and 26 which are critical for receptor binding [Adelhorst K et al., 1994; Gallwitz B et al., 1994]

between 4 and 9, more preferably at pH between 5 and 8 in a concentration between 50-1000 µM, more preferably between 100 and 500 µM and adding less than 50, and preferably less than 25 fold molar excess of linear or branched alkylamino m-PEG with molecular mass between 2 and 60 kDa and 0.1 to 2 U/ml, more preferably 0.2 to 1 U/ml, of M-Tgase and leaving the reaction mixture at temperature between 10 and 50° C., more preferably between 15 and 30° C., for 10 hours or longer. M-Tgase can be, for example, a preparation of Activa WM commercially available from Ajinomoto or a preparation of any natural or recombinant microbial derived M-Tgase with equivalent activity. It is well known that the kinetics of the M-Tgase catalyzed reaction, as of any other enzymatic reaction, can be modulated by temperature and by the amount of enzyme and consequently the reaction time of the above described reactions can be reduced by choosing any convenient combination of enzyme concentration and temperature compatible with the maintenance of catalytic activity. The site-specific monopegylated GLP-1 analogues of the present invention were purified by traditional methods as salting out, dialysis, ultrafiltration, isoelectric precipitation, column chromatography or by their combination and characterized according to methods known in the art and described, for example, in the experimental section. As above reported, no pegylation was obtained when the Tgase catalyzed reactions between GLP-1 analogues and amino functionalized m-PEG were performed in the presence of a preparation of a mammalian Tgase, as shown in tables 1 and 2.

The site-specific monopegylated GLP-1-peptides and analogues showed improved resistance towards enzymatic degradation by DPP-IV studied at 37° C. in vitro, compared to the unmodified peptide. In particular, as shown in table 4, while GLP-1-amide was completely inactivated by cleavage of the N-terminal dipeptide after 8 hours at 37° C., its monopegylated derivative still maintained about 70 percent of active structure even after 24 hour incubation, with GLP-1-amide conjugated to higher molecular weight PEG chains being more resistant to DPP-IV cleavage, as shown in table 4 and FIG. 1.

The monopegylated derivative of Q17N/A24Q-GLP-1 mutant also displayed a similar resistance to in vitro DPP-IV degradation as shown in table 4 and FIG. 1.

TABLE 4

DPP-IV degradation of monopegylated GLP-1-amide derivatives in comparison to GLP-1-amide.

| Product | Degradation % at 24 h |
|---|---|
| GLP-1-amide | 100 (at 8 h) |
| GLP-1-amide-Q17-PEG 20 kDa | 37 |
| GLP-1-amide-Q17-PEG 30 kDa | 25 |
| GLP-1-amide-Q17N/A24Q | 90 |
| GLP-1-amide-Q17N/A24Q-PEG 20 kDa | 41 |

In vivo biological activity of monopegylated GLP-1-peptide derivatives, as assayed in an oral glucose tolerance test carried out in diabetic mice, was evaluated in term of overall glucose-stabilizing capability taking into consideration the following experimental parameters: maximum blood glucose level ($Glu_{max}$ in mg/dl); time to lower the blood glucose level under 100 (±5) mg/dl ($T_{glu<100\ mg/dl}$) and total hypoglycemic degree as percent of saline control ($HD_{\%\ control} = AUC_{saline(0-180)} - AUC_{test(0-180)}/AUC_{saline(0-180)} \times 100$). The results are shown in table 5 and FIG. 2.

TABLE 5

Summary of pharmacodynamic parameters after administration of PEGylated GLP-1 derivatives and Exenatide in diabetic mice

| | GLP-1-amide-Q17-PEG$_{20\ kDa}$ | GLP-1-amide-Q17-PEG$_{30\ kDa}$ | Exenatide |
|---|---|---|---|
| $Glu_{max}$ | 213.9 mg/dl | 167.7 mg/dl | 150.4 mg/dl |
| $T_{glu<100\ mg/dl}$ | 60 min | 60 min | 60 min |
| $HD_{\%\ control}$ | 58.3% | 63.5% | 66.8% |

Glucose related parameters calculated for the first 180 minutes after glucose administration show that both GLP-1-PEG products, in particular GLP-1-PEG$_{30kDa}$, have an activity similar to that of Exenatide, probably due to a comparable DPP-IV resistance.

The glucose-stabilizing activity displayed by 20 kDa and 30 kDa monopegylated GLP-1-amide up to 8 hours after an oral glucose load is possibly due to a combination of increased proteolytic stability and clearance reduction with a final biological efficacy comparable or better than the one displayed by exenatide.

It is a further objective of the present invention to provide pharmaceutically acceptable formulations for the administration of site-specific monoconjugated derivative of GLP-1 like peptides with incretin mimetic properties described in the present invention which are characterized by increased proteolytic stability and/or a longer circulating half-life with respect to non pegylated peptides and are therefore suitable to reduce hyperglycemia with type 2 diabetic patients on the basis of once a day to thrice a week administration.

In these formulations, monopegylated GLP-1 analogues are present in a concentration from 0.1 to 50 mg/ml and wherein said formulations have a pH from 5 to 9, more preferably from 7 to 8. These formulations may further comprise buffer systems with or without addition of tonicity and chelating agents as well as preservatives, stabilizers and surfactants known in the art. In one embodiment of the invention such formulations are aqueous solutions and/or aqueous suspensions while in a further embodiment they are powdered preparations obtained by any acceptable methods, preferably by liophylization.

It is a further objective of the present invention to provide delivery options for the therapeutic application of site-specific monoconjugated derivative of GLP-1 like peptides with incretin mimetic properties described in the present invention which are suitable to reduce hyperglycemia with type 2 diabetic patients on the basis from once a week to twice a month administration through their incorporation in biodegradable polymers or any polymer compositions known in the art for protein and peptide delivery enabling controlled and sustained release of mono-pegylated insulinotropic GLP-1 peptides. Systems for long term delivery of site-specific monoconjugated derivative of GLP-1 like peptides described in the present invention include, among others, organic or inorganic polymeric nano- and micro-particles, liposomes and liposome-like vescicles, lipid nanoparticles, hydrogel-based microparticles, thermo- and pH-responsive polymers and microemulsions known in the art as exemplified by the following basic references: Kohane D S, 2007; Lee K Y and Yuk S H, 2007; Singh S et al., 2007; Jorgensen L et al., 2006; Schmaljohann D, 2006; Muller R H and Keck C M, 2004; Shina V R and Trehan A, 2003, herein incorporated by reference.

A sustained release formulation of monopegylated GLP-1 like peptides with incretin mimetic properties, described as example in the present invention, can be prepared by incorporating the active principle in Poloxamer 407 dissolved in pH 4 acetate buffer at 4° C. The kinetic of in vitro release from a 22% w/w Poloxamer 407 solution containing 0.3 mg/ml of GLP-1-amide Q17-PEG 20 kDA, studied by incubating 1 ml of formulated gel at 37° C. with 1 ml of acetate buffer 0.2 M pH 4.0 is shown in FIG. 3. Poloxamer-based formulations, being able to undergo a transition to a gel phase above 18° C., represent a suitable system for in situ gelation upon subcutaneous injection which is followed by a slow release in the circulation of the monopegylated GLP-1-peptides.

For a better understanding of the present invention the following definitions are provided.

The terms GLP-1 (glucagon-like peptide-1) and GLP-1 analogues according the use of the present invention mean the 30 amino acid C-terminally amidated GLP-1 (SEQ ID No 1), the 31 amino acid C-terminally glycine extended GLP-1 (SEQ ID No 2) and their biologically active forms with deletion, addition or substitution of one or more amino acid residues as well as synthetic or natural insulinotropic peptides with at least 40% sequence identity with respect to human 31 amino acid C-terminally glycine extended GLP-1 of SEQ ID No 2.

Specifically, for the GLP-1-peptide analogues as used herein the term biologically active forms means that the products act as incretin mimetics in that they are able to potentiate glucose-induced insulin secretion when administered in vivo.

The term Q17N-GLP-1 analogues (where Q and N are respectively the one letter code notation for glutamine and asparagine) according the use of the present invention mean GLP-1-amide or C-terminally glycine extended-GLP-1 containing an asparagine residue in position 17 and one single glutamine residue in other positions of the peptidic chain.

Below, some experimental examples are given with the purpose to provide an illustration of the present invention, without constituting a limitation of the field of application thereof.

The terms nano- and micro-particles according to the use of the present invention mean any inorganic and organic polymeric material with dimensions ranging from 10 nanometers to 100 micrometers loaded with a drug in order to achieve a controlled release of the active principle as described, for example, by Kohane D S (2007), Lee K Y and Yukn S H (2007), Muller R H and Keck C M (2004) and Shina V R and Trehan A (2003), herein incorporated by reference.

The term thermoresponsive polymer according to the use of the present invention means any polymeric material whose transition from sol to gel is triggered by an increase in temperature to form an in situ depot drug delivery system as described, for example, by Singh S et al. (2007), Schmalijohann D (2006), herein incorporated by reference.

EXAMPLE 1

Direct Site-Specific Mono-PEGylation of GLP-1 Peptides with m-PEG-Amino 20 kDa, Catalyzed by Microbial Tgase A GLP-1 peptide is dissolved in a 10 mM, pH 8.0 sodium dihydrogen citrate solution at the concentration of 0.5 mg peptide/ml, corresponding to a concentration of about 150 µM. 20 kDa m-PEG-amine (Methoxypolyethylene glycol amine 20000, Iris Biotech) is then added to the peptide solution to achieve a 20:1 PEG:GLP-1 molar ratio. To the reaction mixture, microbial transglutaminase (Activa WM, Ajinomoto), to a final concentration of 0.25 U/ml, is then added. Reaction is carried out under agitation for 16 hours at room temperature.

At the end of reaction, the solution is diluted in a 20 mM, pH 4.0, sodium acetate buffer and purified by ion-exchange column chromatography (Macrocap SP), eluting with a NaCl linear gradient (from 0 to 500 mM in 10 column volumes). The fractions pool containing monopegylated GLP-1 is concentrated, desalted and liophylized. The yield of direct enzyme catalyzed monopegylation of GLP-1 peptides is around 60%.

RP-HPLC of aliquots of reaction mixture withdrawn at times 0 and 16 hours, as well as of purified GLP-1-amide-Q17-PEG 20 kDa are reported in FIG. 4.

EXAMPLE 2

Attempt to Direct Site-Specific Mono-PEGylation of GLP-1-Amide with m-PEG-Amino 20 kDa Catalyzed by Guinea Pig Tgase GLP-1-amide is dissolved in a 50 mM, pH 7.5 TRIS solution at a concentration of 0.5 mg peptide/ml, corresponding to a concentration of about 150 µM.

20 kDa m-PEG-amine (Methoxypolyethylene glycol amine 20000, Fluka) is then added to the protein solution to achieve a 500:1 PEG:G-LP-1 molar ratio.

To the reaction mixture, 0.3 U/ml of guinea pig transglutaminase (Sigma) and 10 mM $CaCl_2$ are then added and the mixture maintained under agitation for 16 hours at room temperature. RP-HPLC performed on the starting and final reaction mixture only showed the presence of unreacted GLP-1-amide with no traces of pegylated derivative.

EXAMPLE 3

Attempt of Direct Site-Specific Mono-Pegylation of S12Q/Q17N GLP-1-Amide with m-PEG-Amino 20 kDa Catalyzed by Microbial Tgase S12Q/Q17N-GLP-1-amide is dissolved in a 10 mM, pH 8.0 sodium dihydrogen citrate solution, at the concentration of 0.5 mg peptide/ml, corresponding to a concentration of about 150 µM.

20 kDa m-PEG-amine (Methoxypolyethylene glycol amine 20000, Iris Biotech) is then added to the peptide solution to achieve a 20:1 PEG:GLP-1 molar ratio. To the reaction mixture, microbial transglutaminase (Activa WM, Ajinomoto), to a final concentration of 0.25 U/ml, is then added. Reaction is carried out under agitation for 16 hours at room temperature. RP-HPLC performed on the starting and final reaction mixture only showed the presence of unreacted S12Q/Q17N-GLP-1-amide with no traces of pegylated derivative.

EXAMPLE 4

Direct Site-Specific Monopegylation of Q17N/A24Q-GLP-1-Amide with m-PEG-Amino 20 kDa Catalyzed by Microbial Tgase Q17N/A24Q-GLP-1-amide is dissolved in a 10 mM, pH 8.0 sodium dihydrogen citrate solution at the concentration of 0.5 mg peptide/ml, corresponding to a concentration of about 150 µM.

20 kDa m-PEG-amine (Methoxypolyethylene glycol amine 20000, Iris Biotech) is then added to the peptide solution to achieve a 20:1 PEG:GLP-1-peptide molar ratio. To the reaction mixture, microbial transglutaminase (Activa WM, Ajinomoto), to a final concentration of 0.25 U/ml, is then added. Reaction is carried out under agitation for 16 hours at room temperature.

At the end of reaction, the solution is diluted in 20 mM, pH 4.0 sodium acetate buffer and purified by column chromatography (Macrocap SP), eluting with a NaCl linear gradient (from 0 to 500 mM in 10 column volumes). The fractions pool containing monopegylated GLP-1 mutant is concentrated, desalted and liophylized. The extent of pegylation reaction as well as the purity of the final monopegylated GLP-1 peptide mutant are checked by RP-HPLC. The yield of direct enzyme catalyzed monopegylation of GLP-1 mutants is around 60%.

EXAMPLE 5

Determination of In Vitro Stability of GLP-1-PEG Derivatives to DPP-IV Digestion Solutions of GLP-1-amide, monopegylated GLP-1-amide or monopegylated GLP-amide mutants or analogues in phosphate buffered saline at a concentration of 0.1 mg/ml (calculated as peptide content equivalent) were mixed with DPP-IV (Dipeptidyl peptidase IV from porcine kidney, Sigma), 5 U/ml of peptide solution and incubated at 37° C. Aliquots of the reaction mixture were withdrawn at different time points and GLP-1-peptide degradation was measured detecting the N-terminal dipeptide His-Ala removed by DPP-IV by RP-HPLC analysis. The enzymatic degradation was calculated from His-Ala title of each sample, as shown for example in FIG. 1

EXAMPLE 6

Determination of In Vitro Biological Activity of GLP-1-Amide, GLP-1 Peptide Analogues and their Monopegylated Derivatives This assay is based on the release of insulin, in the presence of glucose and different concentrations of GLP-1 peptides and their monopegylated derivatives, from RIN-m5f cells derived from insulinoma of rat beta cells. Briefly, $2 \times 10^5$ cells are plated in 6 well plates in complete RPMI medium and incubated at 37° C. for 2 days; cells are washed, incubated 4 more hours with medium with lower glucose concentration (0.2%), then washed again and incubated for 1 hour with a 10 mM solution of GLP-1 peptides or their monopegylated derivatives. Supernatant is harvested and title of released insulin is determined by ELISA assay.

EXAMPLE 7

Determination of In Vivo Biological Activity of GLP-1-Amide-Q17 PEG 5 kDa, GLP-1-Amide-Q17-PEG 20 kDa, GLP-1-Amide-Q17-PEG 30 kDa Evaluation of the stabilizing effects of GLP-1-amide and its pegylated derivatives on plasma glucose were examined using 7 to 10 week old diabetic (db/db) mice. Food was withdrawn for an 18-h period prior to and for 3 hours after oral administration of a glucose solution (1.5 g/kg body weight); food was again withdrawn 6 hours after glucose administration. 40 μg/ml of products to be tested and negative control (phosphate buffered saline) were administered by subcutaneous injection of a volume of 2.5 ml/kg body weight, 30 minutes prior glucose administration. Blood samples were collected from the tail vein of conscious mice before the injection and at 15, 30, 60, 120, 180, 240, 300, 1440 min post injection and glucose concentration was measured by gluco tester Ascensia Elite (Bayer). The results of an experiment carried out with 20 kDa and 30 kDa monopegylated GLP-1.amide in comparison to exenatide and a saline control are shown in FIG. 2.

EXAMPLE 8

Preparation and In Vitro Release Assay of Sustained Release Poloxamer Formulation of GLP-1-Amide-Q17-PEG 20 kDa A 27% solution of Poloxamer 407 was prepared by slowly dissolution of the polymer in 0.2 M acetate buffer pH 4.0 at 4° C. GLP-1-amide-Q17 PEG 20 kDa was added to obtain a final concentration of 0.3 mg/ml of GLP-1-amide-Q17 PEG 20 kDa and 22% Poloxamer and the solution was stored at 4° C.

A dissolution test was performed by incubating 1 ml of formed gel at 37° C. with 1 ml of acetate buffer 0.2 M pH 4.0. Solution was collected and replaced by an equivalent volume of buffer at different time point, in order to evaluate the release of GLP-1-amide-Q 17-PEG 20 kDa by RP-HPLC analysis. Results of dissolution test are shown in FIG. 3

REFERENCES

Adelhorst K, et al. (1994) Structure-activity studies of glucagon-like peptide-1. J. Biol. Chem. 269, 6275-6278

Ando H et al. (1989) Purification and characteristics of a novel transglutaminase derived from microorganisms. Agric. Biol. Chem. 53, 2613-2617

Bloom M. et al. (2003) Albugon fusion protein: a long acting analogue of GLP-1 that provides lasting antidiabetic effect in animal. Diabetes 52 (Suppl. 1), Abstract A112

Buckley D I et al. GLP-1 analogues useful for diabetes treatment. U.S. Pat. No. 5,545,618

Choi S et al. (2004) Control of blood glucose by novel GLP-1 delivery using biodegradable triblock copolymer of PLGA-PEG-PLGA in type 2 diabetic rats. Pharmac. Res. 21, 827-831

Cousson P J et al. (1992) Factors that govern the specificity of transglutaminase-catalysed modification of proteins and peptides. Biochem. J., 282, 929-930

Davidson M B et al. (2005) Exenatide. Nature Rev. Drug Discovery 4, 713-714

Davis F F et al. Non immunogenic polypeptides. U.S. Pat. No. 4,179,337

Delgado C et al. (1992) The uses and properties of PEG-linked proteins, Crit. Rev. Ther. Drug Carrier Syst. 9, 249-304

Drucker D J. (2001) The glucagon-like peptides. Endocrinology 142, 521-527

Eng J et al. (1992) Isolation and characterization of exendin-4, an exendin-3 analogue from *Heloderma suspectum* venom. J. Biol. Chem. 267, 7402-7405

Esposito C, Caputo I (2004) Mammalian transglutaminases. Identification of substrates as a key to physiological function and physiopathological relevance. FEBS J. 272, 615-631

Fontana A et al. (2008) Site specific modification and PEGylation of pharmaceutical proteins mediated by transglutaminase. Adv. Drug Deliv. Rev. 60, 13-28

Fuchsbauer H et al. Bacterial transglutaminases. EP 1068301

Gallwitz B et al. (1994) Structure/activity characterization of glucagon-like peptide-1. Eur. J. Biochem. 225, 1151-1156

Greenwald R B et al. (2003) Effective drug delivery by PEGylated drugs conjugates. Adv. Drug Deliv. Rev. 55, 217-250

Hoist J J. The physiology of glucagon-like peptide 1. Physiol. Rev. 87, 1409-1439, 2007

Johansen L et al. Transglutaminase mediated conjugation of peptides. WO070468

Jorgensen L et al. (2006) Preparing and evaluating delivery systems for proteins. Eur. J. Pharmac. Sci. 29, 174-182

Kaiser E T (1989) Synthetic approaches to biologically active peptides and proteins including enzymes. Acc. Chem. Res. 22, 47-54

Kinstler O B et al. N-terminally chemically modified protein compositions and methods. U.S. Pat. No. 5,985,265

Kinstler O B et al. (1996) Characterization and stability of N-terminally PEGylated rhG-CSF, Pharmac. Res. 13, 996-1002

Knudsen L B et al. GLP-1 derivatives. EP0944648

Knudsen L B et al. (2000) Potent derivatives of glucagon-like-peptide-1 with pharmacokinetic properties suitable for once daily administration. J. Med. Chem. 43, 1664-1669

Kohane D S (2007) Microparticles and nanoparticles for drug delivery. Biotechnol. Bioengn. 96, 203-209

Kobayashi K et al. (1996) Epsilon-(gamma-glutamyl) lysine cross-links of spore coat proteins and transglutaminase activity in Bacillus subtilis. FEMS Microbiol. Lett. 144, 157-160

Kobayashi K et al. (1998) Molecular cloning of the transglutaminase gene from Bacillus subtilis and its expression in Escherichia coli. Biosci. Biotechnol. Biochem. 62, 1109-1114

Lee S H et al. (2005) Synthesis, characterization, and pharmacokinetic studies of PEGylated glucagon-like peptide-1. Bioconjug. Chem. 16, 377-382

Lee K Y, Yuk S H (2007) Polymeric protein delivery systems. Progress Polymer Sci. 32, 669-697

Merrifield B (1986) Solid phase synthesis. Science 232, 241-247

Muller R H, Keck C M (2004) Challenges and solutions for the delivery of biotech drugs. A review of drug nanocrystal technology and lipid nanoparticles. J. Biotechnol. 113, 151-170

Nucci M L et al. (1991) The therapeutic value of poly(ethylene glycol)-modified proteins, Adv. Drug Deliv. Rev. 6, 133-151

Ohtsuka T et al. (2000) Substrate specificities of microbial transglutaminase for primary amines, J. Agric. Food Chem. 48, 6230-6233

Ohtsuka T et al. (2000) Comparison of substrate specificities of transglutaminase using synthetic peptides as acyl donors. Biosci. Biotechnol. Biochem., 64, 2608-2613

Parveen S, Sahoo S K (2006) Clinical application of polyethylene glycol conjugated proteins and drugs. Clin. Pharmacokinet. 45, 965-988

Pastor M T et al. (1999) Addressing substrate glutamine requirements for tissue transglutaminase using substance P analogues. FEBS Lett. 451, 231-2134

Ritzel U et al. (1998) A synthetic glucagon-like peptide-1 analog with improved plasma stability. J. Endocrinol. 158, 93-102

Roberts M J et al. (2002) Chemistry for peptide and protein PEGylation, Adv. Drug Deliv. Rev. 54, 459-476

Sambrock J et al. (1989) Molecular Cloning. A laboratory manual, 2$^{nd}$ edition, Cold Spring Harbor Laboratory Press Sato H et al. (2000) Transglutaminase-mediated dual and site-specific incorporation of poly(ethylene glycol) derivatives into a chimeric interleukin-2. Bioconjug. Chem. 11, 502-509

Sato H (2002) Enzymatic procedure for site-specific pegylation of proteins. Adv. Drug Deliv. Rev. 54, 487-504

Schmaljohann D (2006) Thermo- and pH-responsive polymers in drug delivery. Adv. Drug. Deliv. Rev. 58, 1655-1670

Schnabel C A et. (2006) Immunogenicity of xenopeptide hormone therapy. Peptides 27, 1902-1910

Shina V R, Trehan A (2003) Biodegradable microspheres for protein delivery. J. Control. Rel. 90, 261-280

Singh S et al. (2007) Thermosensitive polymers: Synthesis, characterization, and delivery of proteins. Internat. J. Pharmac. 341, 68-77

Takahara Y. Modification of peptide and protein. EP785276

Takahara Y et al. Modification of peptide and protein. U.S. Pat. No. 6,010,871

Veronese et al. Novel G-CSF conjugates WO2005099769

Thornton K, Gorenstein D G (1994) Structure of glucagon-like peptide (7-36) amide in a dodecylphosphocholine micelle as determined by 2D NMR. Biochemistry 33, 3532-3539

Uçkaya G et al. (2005) Improvement of metabolic state in an animal model nutrition-dependent typ 2 diabetes following treatment with S 23521, a new glucagon-like peptide 1 (GLP-1) analogue. J. Endocrinol. 184, 503-513

Yokoyama K et al. (2000) Overproduction of microbial transglutaminase in Escherichia coli, in vitro refolding and characterization of the refolded form. Biosci. Biotechnol. Biochem. 64, 1263-1270, 2000

Youn Y S et al. (2007) Evaluation of therapeutic potentials of site-specific PEGylated glucagon-like peptide-1 isomers as type 2 anti-diabetic treatment. Insulinotropic activity, glucose-stabilizing capability and proteolytic stability. Biochem. Pharmacol. 73, 84-93

Zalipski S (1995) Chemistry of polyethylene glycol conjugates with biologically active molecules, Adv. Drug Deliv. Rev. 16, 157-182

The invention claimed is:

1. A monoconjugated derivative of an incretin mimetic peptide comprising the amino acid sequence set forth in SEQ ID NO:1 or SEQ ID NO:2 and analogues thereof wherein:
   i) the glutamine residue at position 17 is covalently and directly linked to an alkylamino functionalized polymer; or
   ii) the glutamine at position 17 is replaced by an asparagine and the alanine at position 24 is replaced by a glutamine and which glutamine at position 24 is covalently and directly linked to an alkylamino functionalized polymer.

2. The monoconjugated derivative of claim 1, wherein the alkylamino functionalized polymer is a linear or branched monomethoxy-poly(ethylene glycol).

3. The monoconjugated derivative of claim 2, wherein the linear or branched monomethoxy-poly(ethylene glycol) is functionalized with a primary amino group.

4. The monoconjugated derivative of claim 3, wherein the linear or branched monomethoxy-poly(ethylene glycol) functionalized with a primary amino group exhibits a molecular weight from 2 to 50 kDa.

5. The monoconjugated derivative of claim 4, wherein the linear or branched monomethoxy-poly(ethylene glycol) functionalized with a primary amino group exhibits a molecular weight from 5 to 40 kDa.

6. The monoconjugated derivative of claim 4, wherein the linear or branched monomethoxy-poly(ethylene glycol) functionalized with a primary amino group exhibits a molecular weight from 10 to 30 kDa.

7. The monoconjugated derivative of claim 4, wherein the linear or branched monomethoxy-poly(ethylene glycol) functionalized with a primary amino group exhibits a molecular weight from 15 to 25 kDa.

8. The monoconjugated derivative of claim 4, wherein the linear or branched monomethoxy-poly(ethylene glycol) functionalized with a primary amino group exhibits a molecular weight of about 20 kDa.

9. A method for treating diabetes in a human or animal subject afflicted with diabetes comprising administering a therapeutically effective amount of the monoconjugated derivative of claim 1 to the human or animal subject.

10. The method of claim 9, wherein the diabetes is type 2 diabetes.

11. A method for reducing hyperglycemia in patients afflicted with diabetes comprising administering a therapeutically effective amount of the monoconjugated derivative of claim 1 to the patient afflicted with diabetes.

12. The method of claim 11, wherein the diabetes is type 2 diabetes.

13. A formulation comprising the monoconjugated derivative of claim 1 and at least a pharmaceutically acceptable excipient and/or adjuvant.

14. A formulation comprising the monoconjugated derivative of claim 1 and polymeric and/or lipidic nano- and microparticles.

15. A formulation comprising the monoconjugated derivative of claim 1 and a thermoresponsive polymer.

* * * * *